United States Patent [19]

Osypka

[11] Patent Number: 5,234,451
[45] Date of Patent: Aug. 10, 1993

[54] APPARATUS FOR ELIMINATING OCCLUSIONS AND STENOSES IN BODY CAVITIES

[76] Inventor: Peter Osypka, Basler Strasse 109, Grenzach-Wyhlen, Fed. Rep. of Germany

[21] Appl. No.: 794,111

[22] Filed: Nov. 15, 1991

[30] Foreign Application Priority Data

Nov. 16, 1990 [DE] Fed. Rep. of Germany ....... 4036570

[51] Int. Cl.⁵ ............................................ A61B 17/36
[52] U.S. Cl. ...................................... 606/159; 606/171
[58] Field of Search ................ 604/22; 606/127, 128, 606/159, 169, 171

[56] References Cited

U.S. PATENT DOCUMENTS

| | | | |
|---|---|---|---|
| 3,749,085 | 7/1973 | Willson et al. | 606/159 |
| 3,927,675 | 12/1975 | Pohlman | 606/128 |
| 4,605,003 | 8/1986 | Oinuma et al. | 606/128 |
| 4,728,319 | 3/1988 | Masch | 604/22 |
| 4,749,376 | 6/1988 | Kensey et al. | 606/159 |
| 4,784,636 | 11/1988 | Rydell | 606/159 |
| 4,923,462 | 5/1990 | Stevens | 604/22 |
| 4,936,845 | 6/1990 | Stevens | 606/159 |
| 4,994,067 | 2/1991 | Summers | 606/170 |
| 5,026,384 | 6/1991 | Farr et al. | 606/180 |

FOREIGN PATENT DOCUMENTS

| | | |
|---|---|---|
| 0177782 | 4/1986 | European Pat. Off. . |
| 0316796 | 5/1989 | European Pat. Off. . |
| 326151 | 10/1973 | Fed. Rep. of Germany . |
| 3802550 | 8/1988 | Fed. Rep. of Germany . |
| 805709 | 9/1988 | Fed. Rep. of Germany . |
| 3419962 | 3/1990 | Fed. Rep. of Germany . |
| 2645009 | 10/1990 | France . |
| 9009762 | 9/1990 | PCT Int'l Appl. ................. 606/127 |

*Primary Examiner*—Ralph Lewis
*Attorney, Agent, or Firm*—Peter K. Kontler

[57] ABSTRACT

Apparatus for eliminating or reducing occlusions or stenoses in veins and other body cavities has an elongated catheter with an ellipsoidal distal end having an internal anvil cooperating with a reciprocable hammer at the distal end of a flexible probe to drive the distal end of the catheter into an occlusion or into a stenoses. The proximal end of the probe is connected to the output element of a reciprocating unit which can be combined with a device for rotating the probe and/or the catheter. The distal end of the probe can be provided with an extension which projects beyond the hammer and beyond the distal end of the catheter to act upon a stenosis or upon an occlusion ahead of the distal end of the catheter.

19 Claims, 2 Drawing Sheets

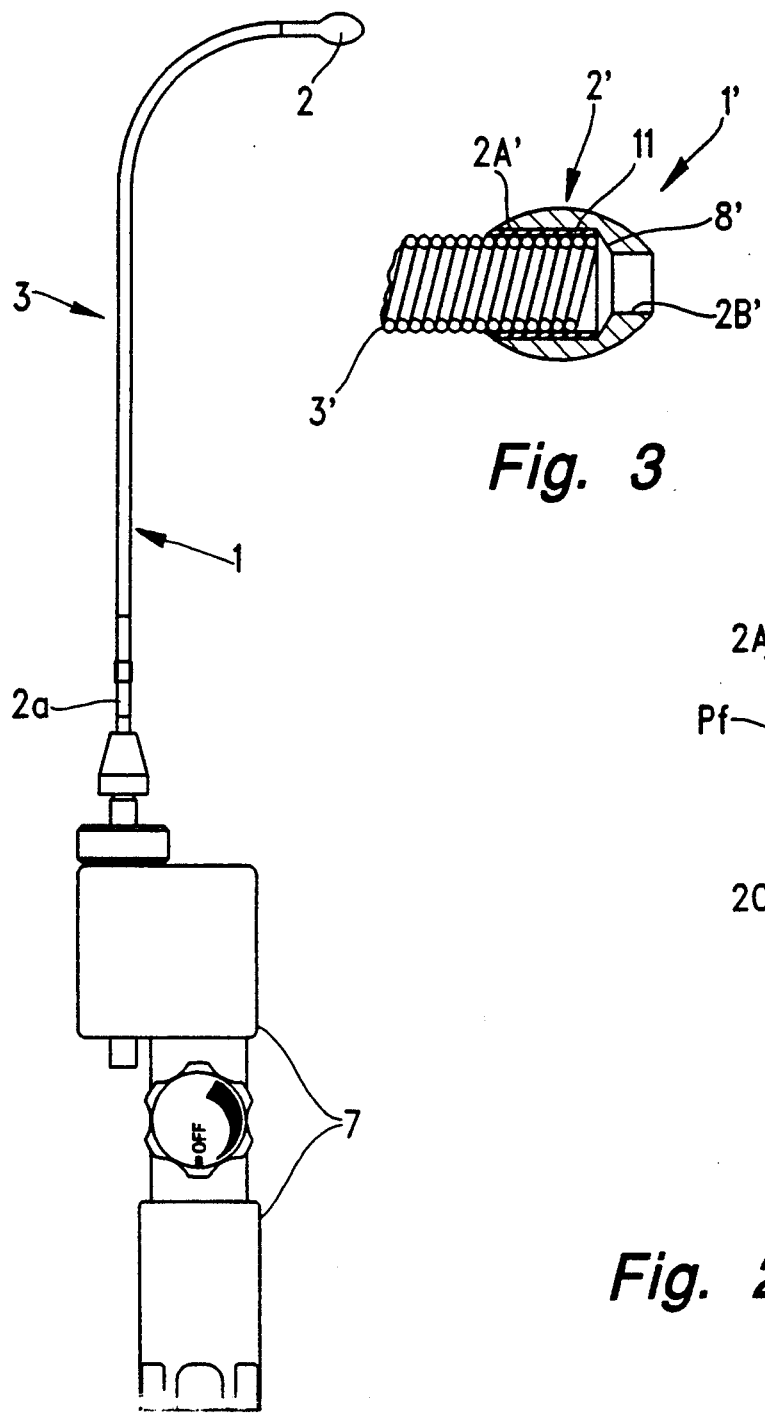
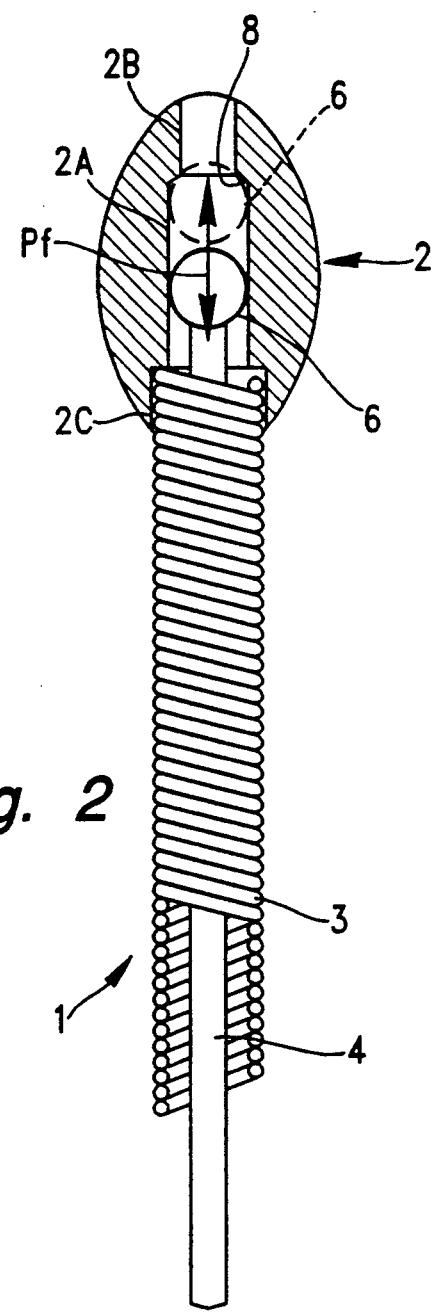
Fig. 1
Fig. 2
Fig. 3

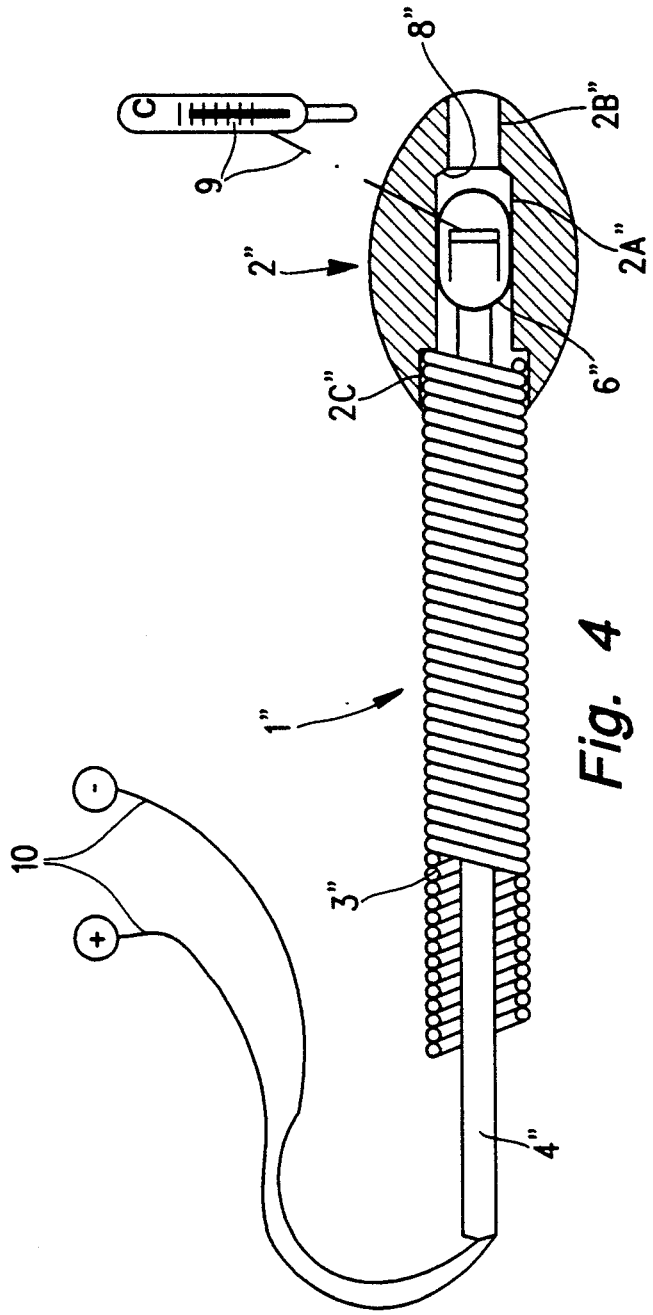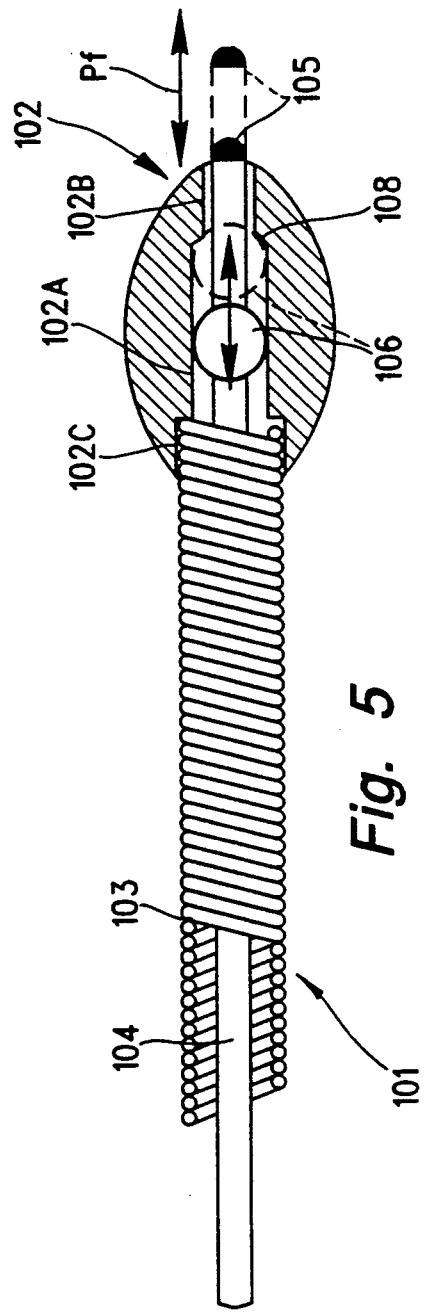

APPARATUS FOR ELIMINATING OCCLUSIONS AND STENOSES IN BODY CAVITIES

BACKGROUND OF THE INVENTION

The invention relates to improvements in apparatus for acting upon (particularly for reducing or eliminating) occlusions and stenoses in veins and other body cavities, such as intravascular blockages.

Certain heretofore known apparatus for the treatment of stenoses employ balloons which are inflated subsequent to introduction of a balloon carrier, such as a catheter, into the body cavity. The balloon constitutes or is affixed to the distal end of the catheter and is inflated when the distal end of the catheter reaches an occlusion or a stenosis. A drawback of such apparatus (reference may be had, for example, to German Utility Model No. G 88 05 709.7 of Angiomedics, published Sep. 15, 1988) is that the balloon cannot be introduced into a very narrow constriction and cannot penetrate into an occlusion in a relatively narrow blood vessel or another body cavity.

It was also proposed to employ a rotary catheter, particularly for reopening of occluded blood vessels. An advantage of apparatus which employ a rotary catheter is that the distal end of the rotary catheter can be more readily introduced into a body cavity than a catheter which is merely pushed into the cavity but does not rotate about its longitudinal axis. The reason is that the friction between the distal end of a rotary catheter and the wall surrounding a body cavity which is to receive the catheter is much less pronounced than when a non-rotating catheter is forced into a body cavity. The rotary catheter has an olive-shaped or a similar substantially ellipsoidal distal end which is caused to penetrate into an obstruction in a body cavity and to enlarge the passage as the rotating catheter continues to advance. Such enlargement involves displacement and compression of material which surrounds an obstruction. The substantially ellipsoidal distal end of the rotating catheter seeks the path of least resistance and thus advances, or is expected to advance, into and through the still unsealed portion of the passage within a stenosis or into that (normally central) part of an occlusion which was last to develop.

It is also known to confine a rotary catheter in a second or protective catheter which does not or need not rotate. The purpose of the second catheter is to prevent undue flexing of the normally highly flexible rotary catheter. Such prevention of undue flexing is desirable and advantageous because, when properly guided, the rotary catheter is more likely to rapidly advance toward the situs of an occlusion or stenosis. However, the non-rotating second catheter also exhibits certain serious drawbacks. Thus, the two catheters define an annular clearance which is rapidly filled with blood or with another body fluid, and such fluid opposes (and can prevent) rotation of the inner catheter.

Another drawback of conventional apparatus which employ rotary catheters is that the rotary catheter must be highly flexible in order to avoid puncturing of and/or other damage to the wall surrounding a blood vessel or another body cavity. On the other hand, if the apparatus is to treat an occlusion which contains a very hard substance (such as plaque), the occlusion cannot be successfully attacked by resorting to a highly flexible rotary catheter. In fact, the rotary catheter is often incapable of successfully acting upon an occlusion or a stenosis even if it is stiffened by a second or outer catheter which is not rotated during introduction into a blood vessel or into another body cavity.

European patent application No. 0 316 796 of DonMichael et al. (published May 24, 1989) discloses an intravascular ultrasonic catheter probe which employs a wire with a bulbous tip at the distal end. The proximal end of the wire is connected with an ultrasonic energy source, and the major part of the wire is confined in a hollow catheter. The distal end of the wire is retracted into the catheter during introduction into a blood vessel, and the bulbous distal end is thereupon expelled from the distal end of the catheter to act upon a stenosis while the energy source is active to vibrate the wire. The distal end of the wire is necessarily small because it must be capable of passing through the catheter. A small distal end is likely to perforate and/or otherwise damage the wall surrounding a body cavity.

German patent application No. 38 02 550 of Borodulin et al. (published Aug. 11, 1988) discloses a vibratory probe within a deformable bulbous distal end of a catheter. The distal end of the probe repeatedly expands the distal end of the catheter radially and axially to thus push a foreign body (such as a stone) through the body cavity. The apparatus of Borodulin can shift mobile foreign bodies in a urinary tract or in another body cavity but is highly unlikely to successfully attack a stenosis or an occlusion in a blood vessel because the radially and axially expandable bulbous distal end of the catheter is actually a balloon which is too soft to be useful in connection with the treatment of stenoses and/or occlusions.

German Pat. No. 34 19 962 to Okada (granted Mar. 1, 1990) discloses a high-frequency incision and excision apparatus which is designed for removal of polyps and operates with a wire loop.

European patent application No. 0 177 782 of Auth (published Apr. 16, 1986) discloses a transluminal thrombectomy apparatus wherein a drive shaft is rotated to withdraw the fibrin of the thrombus and to thus establish a path for the flow of blood. The major part of the shaft is confined in a flexible tubular housing.

German Utility Model No. G 73 26 151.5 of Wolf (published Oct. 4, 1973) discloses an endoscopic coagulation probe wherein a hollow metallic head is inserted into the distal end of a flexible hose and is filled with a heat-resistant material. The heat-resistant material confines an electric heating element for the head, and the conductors connecting such heating element with an energy source extend from the distal end to the proximal end of the hose. The hose can be replaced with a tube.

OBJECTS OF THE INVENTION

An object of the invention is to provide an apparatus which is capable of effectively reducing or eliminating occlusions or stenoses in body cavities without the danger of perforating and/or otherwise damaging the walls surrounding the affected body cavities.

Another object of the invention is to provide a novel and improved method of imparting movements to the distal end of a catheter in the above outlined apparatus.

A further object of the invention is to provide a novel and improved distal end for a flexible probe which is used in the above outlined apparatus.

An additional object of the invention is to provide a novel and improved distal end for the catheter of the above outlined apparatus.

Still another object of the invention is to provide a novel and improved combination of distal ends of the catheter and probe in the above outlined apparatus.

An additional object of the invention is to provide a novel and improved method of moving the distal end of the catheter and/or the distal end of the probe in the course of a treatment involving a reduction or elimination of stenosis or occlusion in a body cavity.

Another object of the invention is to enhance the ability of the distal end of a probe and/or of the distal end of a catheter to successfully eliminate or reduce stenoses and/or occlusions in blood vessels or other body cavities.

An additional object of the invention is to provide an apparatus wherein the distal end of the catheter and/or the distal end of the probe can be rapidly exchanged and wherein such distal ends can establish a path for the flow of a body fluid into the catheter or a path for the flow of a flowable material from the catheter into the body cavity.

A further object of the invention is to provide an apparatus which is more versatile than heretofore known apparatus for elimination or reduction of stenoses, occlusions and/or other obstructions in blood vessels and/or other body cavities.

SUMMARY OF THE INVENTION

The invention is embodied in an apparatus for treating (particularly for eliminating) occlusions and stenoses in blood vessels and/or other body cavities. The improved apparatus comprises an elongated flexible hollow catheter having a proximal end and a distal end which is provided with an internal anvil, an elongated flexible probe which is received in the catheter and has a proximal end and a distal end provided with a hammer adjacent the internal anvil, and means for imparting to the probe movements so as to cause the hammer to repeatedly strike the anvil and to thereby drive the distal end of the catheter deeper into a body cavity into which the catheter is inserted. The means for imparting movements preferably includes means for reciprocating the hammer toward and away from the proximal end of the catheter. The reciprocating means is or can be connected with the proximal end of the probe.

The distal end of the probe can further comprise an extension projecting beyond the hammer and designed to project beyond the distal end of the catheter. The distal end of the catheter can constitute or resemble a bulb. The maximum dimension of the extension (as measured transversely of the catheter) is less than the maximum transverse dimension of the preferably ellipsoidal distal end of the catheter.

The extension can consist, at least in part, of a hard material, e.g., diamond dust.

The means for imparting movements can further comprise means for rotating at least one of the distal ends, for example, the distal end of the probe or the distal end of the catheter.

The reciprocating means can include means for reciprocating the hammer at an amplitude of between approximately 0.5 and 5 mm, preferably between approximately 1 and 2 mm.

The means for imparting movements can include at least one motor, at least one electromagnetic vibrator or at least one ultrasonic generator.

The apparatus can further comprise a temperature sensor in and/or means for supplying ultrasonic energy to the distal end of the probe.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a schematic elevational view of an apparatus which embodies one form of the invention;

FIG. 2 is an enlarged partly sectional view of the distal ends of the catheter and probe in the apparatus of FIG. 1;

FIG. 3 is a partly sectional view of the distal end of a modified catheter;

FIG. 4 is a fragmentary partly elevational, partly sectional and partly schematic view of a third apparatus; and FIG. 5 is a similar view of a further apparatus.

DESCRIPTION OF PREFERRED EMBODIMENTS

Referring first to FIGS. 1 and 2, there is shown an apparatus 1 which can be utilized to eliminate occlusions or stenoses in blood vessels and/or other body cavities. The improved apparatus comprises an elongated flexible tubular catheter 3 of convoluted wire, an elongated flexible probe 4 which is confined in the catheter 3, and a unit 7 which serves to impart movements to the catheter 3 and/or to the probe 4. The catheter 3 has a substantially ellipsoidal or partly ellipsoidal distal end 2 and a proximal end 2a which is separably connected to the unit 7. The distal end of the probe 4 includes a substantially spherical hammer 6 which is received in the median portion 2A of an elongated passage in the distal end 2, and the probe 4 further includes a proximal end (not specifically shown) which is connected with one or more output elements of the unit 7. The output element (or the one output element) of the unit 7 serves to impart to the probe 4 reciprocatory movements in directions which are indicated by a double-headed arrow Pf in order to cause the hammer 6 at the distal end of the probe to repeatedly strike against an internal shoulder 8 (hereinafter called anvil) of the distal end 2. The anvil 8 is located between the median portion 2A and the front or distal portion 2B of the aforementioned passage in the distal end 2. Such passage further includes a rear or proximal portion 2C which serves to receive the foremost convolutions of the wire which constitutes the main portion of the catheter 3. The foremost convolutions of the wire can be glued, welded or otherwise reliably secured to the distal end 2 of the catheter 3.

When the unit 7 is in operation to impart to the probe 4 a reciprocatory movement in directions which are indicated by the arrow Pf, the hammer 6 strikes the anvil 6 at a relatively high frequency and at an amplitude of preferably 0.5 to 5 mm (for example, at an amplitude of 1 to 2 mm) in order to drive the ellipsoidal distal end 2 into an obstruction (e.g., into a stenosis or an occlusion) in a body cavity into which the catheter has been introduced in a manner well known from the art and forming no part of the present invention. The maximum transverse dimension (as measured transversely of the major portion of the catheter 3) of the distal end 2 is selected in dependency on the dimensions of the body cavity into which the components 3, 4 of the apparatus 1 are to be introduced and on the nature of the obstruction (occlusion or stenosis) which is to be eliminated or reduced. In the embodiment of FIGS. 1 and 2, the maximum transverse dimension of the distal end 2 is approximately twice the outer diameter of the major portion of the catheter 3.

FIG. 3 shows a portion of a modified apparatus 1' wherein the distal end 2' of the catheter 3' comprises a passage including a first portion 2A' and a second portion 2B'. The anvil 8' is located between the two portions 2A', 2B' of the passage and the portion 2A' receives a thermally and/or electrically insulating sleeve 11 which, in turn, snugly receives the foremost convolutions of the wire constituting the major portion of the catheter 3'. The passage of the distal end 2 or 2' serves to permit evacuation of blood and/or other body fluids when the apparatus of the present invention is in use.

FIG. 4 shows a portion of a third apparatus 1". All such parts of the apparatus 1" which are identical with or clearly analogous to corresponding parts of the apparatus 1 of FIGS. 1 and 2 are denoted by similar reference characters each followed by two primes. The Hammer 6" at the distal end of the probe 4" has an elongated shape and is reciprocable in the median portion 2A" of the passage in the ellipsoidal distal end 2" of the catheter 3" to repeatedly strike against the internal shoulder 8" between the portions 2A" and 2B" of the passage. The hammer 6" is equipped with a suitable temperature sensor 9 which can be provided with a scale to facilitate observation of the temperature in the passage 2A"-2C" while the apparatus 1" is in use. The probe 4" is further connected with a source 10 of high-frequency energy which can be supplied at a rate required to maintain the distal end 2" at a required optimum temperature in actual use of the apparatus 1". Thus, a stenosis or an occlusion can be treated by mechanical means (by causing the distal end 2" to repeatedly impact against an obstruction in a body cavity) as well as (simultaneously or exclusively) by heat, i.e., as a result of maintaining the distal end 2" at an optimum temperature for a particular treatment. The application of heat is often desirable in order to smoothen the internal surface bounding the body cavity which receives the distal end 2". The treatment with a heated distal end is particularly effective if the catheter 3" is rotated by the unit 7 or by another suitable torque transmitting unit. Thus, the treatment can involve impact drilling (hammer 6" strikes the anvil 8"), rotational drilling (catheter 3" and/or distal end 2" are caused to rotate about the longitudinal axis of the catheter) and/or heating to a desired temperature (by the high-frequency generator 10 or in any other suitable way). As mentioned above, the smoothing action of the heated distal end 2" is particularly effective if such distal end is rotated while the apparatus 1" is in actual use.

An advantage of the apparatus of FIGS. 1-2, 3 and 4 is that the unit 7 indirectly reciprocates the distal end 2, 2' or 2" of the catheter 3 and that the relatively small hammer 6, 6' or 6" at the distal end of the probe need not directly engage an occlusion or a stenosis. This reduces the danger of perforating the wall surrounding a body cavity because such wall is contacted only by the substantially ellipsoidal distal end 2, 2' or 2" whose transverse dimensions are or can be a multiple of those of the distal end of the probe.

FIG. 5 shows a further apparatus 101. All such parts of this apparatus which are identical with or analogous to the corresponding parts of the apparatus 1 of FIGS. 1 and 2 are denoted by similar reference characters plus 100. The distal end of the probe 104 comprises a spherical hammer 106 and a smaller-diameter extension 105 which projects through the front portion 102B of the passage 102A-102C and is reciprocable in the directions of double-headed arrow Pf, together with the hammer 106 and the remaining parts of the probe 104, between the solid-line and broken-line positions of FIG. 5. Thus, an obstruction in a body cavity can be treated first by the extension 105 and thereupon by the distal end 102. At least a portion of the extension 105 preferably consists of a relatively hard or very hard material; for example, the substantially hemispherical head of the extension 105 can be coated with diamond dust. This ensures that the extension 105 can effectively displace hard accumulations of plaque or the like.

The maximum transverse dimension of the extension 105 can be a small or a minute fraction of the maximum transverse dimension of the substantially ellipsoidal distal end 102 of the catheter 103. This has been found to be highly advantageous in connection with the treatment of certain types of occlusions or stenoses. The extension 105 moves between the two end positions while the hammer 106 repeatedly moves into and from impact-transmitting engagement with the internal anvil 108 of the distal end 102. The extension 105 and the distal end 102 operate in series to thus ensure a multiple-stage treatment of an occlusion or a stenosis in a blood vessel or in another body cavity.

The unit 7 is preferably designed to apply to the probe 4, 4', 4" or 104 a rotary and/or a reciprocatory movement. In addition, the unit 7 is preferably designed to impart (when necessary) a rotary movement to the distal end 2, 2', 2" or 102. The arrangement is or can be such that the unit 7 is adjustable to impart to the probe a reciprocatory movement (as indicated by the arrows Pf) at a selected frequency and/or amplitude, to impart to the probe a combined reciprocatory and rotary movement, or to impart to the probe a rotary and/or reciprocatory movement and to simultaneously impart a rotary movement to the corresponding catheter 3, 3', 3" or 103. This contributes to versatility of the improved apparatus. It is further possible to furnish the apparatus with several motion transmitting units, e.g., with a unit which is designed to merely reciprocate the probe, with a unit which is designed to reciprocate and rotate the probe, and with a unit which can rotate and/or reciprocate the probe and can also rotate the catheter. The selection and number of various movements of the catheter and/or probe depends on the nature of the obstruction which is to be acted upon by the distal end of the catheter and/or by the distal end of the probe when the improved apparatus is in actual use. It is further within the purview of the invention to utilize a unit 7 or an analogous unit which can reciprocate the probe and is capable of simultaneously rotating the distal end of the catheter.

One presently preferred use of the improved apparatus is to treat thromobosed coronary arteries or other blood vessels. The properly introduced distal end of the catheter acts not unlike an impact drill in that its internal anvil receives repeated impulses from the hammer at the distal end of the probe. If the apparatus is of the type shown in FIG. 5, the extension 105 acts as a supplementary drilling tool which acts upon undesirable accumulations in a body cavity ahead of the distal end 102.

An advantage of the improved apparatus is that the major part of or the entire probe is confined in the catheter. This ensures that the major part of the probe, or the entire probe, is prevented from contacting the wall surrounding a body cavity, and its reciprocatory movements in response to actuation of the unit 7 are at least substantially unimpeded. This, in turn, ensures that the hammer 6, 6', 6" or 106 at the distal end of the probe transmits to the associated anvil blows of a selected magnitude. Such blows can be selected by appropriate adjustment of the unit 7 which, as already mentioned above, is or can be designed to permit variations of the amplitude and/or frequency of reciprocatory movement of the probe.

A further advantage of the improved apparatus is its versatility. For example, if the unit 7 is designed to rotate the catheter and its distal end while simultaneously reciprocating the probe, the distal end of the catheter acts not unlike an impact drill while also exhibiting the advantages of a rotary catheter. This is often of particular advantage when the improved apparatus is utilized to act upon hard (e.g., calcified) or extremely hard occlusions in body cavities. Such occlusions can be acted upon even more effectively if the apparatus is designed in a manner as shown in FIG. 5 and the unit 7 is designed to rotate the catheter 103 and its distal end 102 as well as the probe 104 with distal end 105+106. This ensures a highly effective treatment of old and very hard occlusions by causing the material of such occlusions to yield radially of the distal ends of the catheter and probe and to permit the establishment of a path for the flow of blood or another body fluid.

The stroke or amplitude of the hammer of the probe will be selected in dependency upon the nature of the occlusion or stenosis which necessitates treatment.

The exact construction of the unit 7 forms no part of the present invention. Such unit can employ one or more electric motors (e.g., in combination with one or more eccentrics), one or more electromagnetic vibrators or an ultrasonic generator. The selection will be made in dependency upon the desired versatility of the unit 7, upon the desired range of amplitudes of the hammer, upon the desired frequency of the probe and/or upon the desired rotational speed of the probe and/or catheter.

The improved apparatus is susceptible of many additional modifications without departing from the spirit of the invention. For example, the hammer 6" of FIG. 4 can be equipped with an electric heating element which is connected to a suitable energy source by conductor means, not shown. The major part of the probe 4" can be electrically insulated but the hammer 6" (which contains or carries the sensor 9) is not insulated. This renders it possible to heat the hammer 6" (and hence the distal end 2") to a desired temperature by resorting to the source of high-frequency energy 10 or in another suitable way. Proper heating of the distal end 2" renders it possible to smoothen the wall around a body cavity which contains an occlusion or a stenosis without injuring the wall. The heating and smoothing action can be carried out while the hammer 6" is in the process of repeatedly striking the anvil 8" or thereafter. Furthermore, the catheter 3" and its distal end 2" can be rotated during heating of the distal end 2".

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for treating occlusions and stenoses in body cavities, comprising an elongated flexible hollow catheter having a proximal end and a distal end provided with an internal anvil; an elongated flexible probe received in said catheter and having a proximal end and a distal end including a hammer adjacent said internal anvil; and means for imparting to said probe movements to cause said hammer to repeatedly strike against the anvil, including alternating reciprocatory movements into and completely out of contact with the anvil, and to thereby drive the distal end of the catheter deeper into the body cavity into which the distal end of the catheter is inserted.

2. The apparatus of claim 1, wherein said means for imparting movements includes means for reciprocating said hammer toward and away from the proximal end of said catheter, said reciprocating means being connected with the proximal end of said probe.

3. The apparatus of claim 2, wherein the distal end of said probe further comprises an extension projecting beyond said hammer and beyond the distal end of said catheter.

4. The apparatus of claim 3, wherein the distal end of said catheter at least resembles an ellipsoid.

5. The apparatus of claim 3, wherein said extension has a first maximum dimension, as measured transversely of said catheter, and said distal end of said catheter has a greater second maximum transverse dimension.

6. The apparatus of claim 3, wherein said extension comprises a hard material.

7. The apparatus of claim 6, wherein said hard material is diamond dust.

8. The apparatus of claim 3, wherein said means for imparting movements further comprises means for rotating at least one of said distal ends.

9. The apparatus of claim 8, wherein said means for rotating includes means for rotating the distal end of said probe.

10. The apparatus of claim 2, wherein said means for imparting movements further comprises means for rotating at least one of said distal ends.

11. The apparatus of claim 2, wherein said means for imparting movements further comprises means for rotating the distal end of said catheter.

12. The apparatus of claim 2, wherein said reciprocating means includes means for reciprocating said hammer at an amplitude of between approximately 0.1 and 5 mm.

13. The apparatus of claim 12, wherein said amplitude is between approximately 1 and 2 mm.

14. The apparatus of claim 1, wherein said means for imparting movements is connected with the proximal end of said probe.

15. The apparatus of claim 1, wherein said means for imparting movements includes at least one motor connected to the proximal end of said probe.

16. The apparatus of claim 1, wherein said means for imparting movements includes at least one electromagnetic vibrator connected to the proximal end of said probe.

17. The apparatus of claim 1, wherein said means for imparting movements includes at least one ultrasonic generator connected to the proximal end of said probe.

18. The apparatus of claim 1, further comprising a temperature sensor in the distal end of said probe to ascertain the temperature of the distal end of said catheter.

19. The apparatus of claim 1, further comprising means for supplying high frequency energy to the distal end of said probe, said energy supplying means being connected to the proximal end of said probe.

* * * * *